(12) United States Patent
Behrend et al.

(10) Patent No.: US 8,725,227 B2
(45) Date of Patent: *May 13, 2014

(54) ELECTRODE ARRANGEMENT AND MEASURING DEVICE FOR MEASURING THE ELECTRICAL ACTIVITY IN AN ELECTRICALLY ACTIVE TISSUE

(75) Inventors: Detlef Behrend, Rostock-Warnemünde (DE); Klaus-Peter Schmitz, Rostock-Warnemünde (DE); Hans Wilhelm Pau, Rostock (DE); Katrin Sternberg, Rostock (DE); Wolfram Schmidt, Rostock (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 365 days.

This patent is subject to a terminal disclaimer.

(21) Appl. No.: 12/601,156

(22) PCT Filed: Jun. 4, 2008

(86) PCT No.: PCT/EP2008/056944
§ 371 (c)(1),
(2), (4) Date: Apr. 12, 2010

(87) PCT Pub. No.: WO2008/148822
PCT Pub. Date: Dec. 11, 2008

(65) Prior Publication Data
US 2011/0282177 A1 Nov. 17, 2011

(30) Foreign Application Priority Data
Jun. 5, 2007 (DE) .......................... 10 2007 026 645

(51) Int. Cl.
*A61B 5/0492* (2006.01)
*A61F 11/00* (2006.01)

(52) U.S. Cl.
USPC ............................ 600/373; 600/379; 600/546

(58) Field of Classification Search
USPC .......... 600/379, 373, 382, 546, 559; 607/116, 607/136, 137, 118
See application file for complete search history.

(56) References Cited

U.S. PATENT DOCUMENTS

| 4,590,946 A | 5/1986 | Loeb ............................. 600/375 |
| 5,400,784 A * | 3/1995 | Durand et al. ................ 600/377 |

(Continued)

OTHER PUBLICATIONS

International Bureau of WIPO, International Search Report, PCT/EP2008/056944, dated Jan. 2, 2010.

*Primary Examiner* — Lee S Cohen
*Assistant Examiner* — Erin M Cardinal
(74) *Attorney, Agent, or Firm* — Sunstein Kann Murphy & Timbers LLP

(57) ABSTRACT

The invention relates to an electrode arrangement and a measuring device for measuring the action flow and/or the action potential of an electrically active tissue. The aim of the invention is to provide a simple and economically producible electrode for measuring action flows and/or action potentials in electrically active tissues (preferably the stapedius muscle tissue), ensuring that the electrode is fixed securely, but reversibly, in the muscle tissue and that the muscle tissue is disturbed as little as possible. The electrode arrangement according to the invention comprises a first electrode (2) and a fixing element (3), the first electrode (2) being connected to a first, long electrical line (4) and consisting of a long base body (6) comprising a first end (7) and a second end (8). The first electrical line (4) is connected to the base body (6) in the region of the second end (8) thereof, and means are provided for reversibly fixing the fixing element (3) to the first electrode (2).

9 Claims, 5 Drawing Sheets

(56) References Cited

U.S. PATENT DOCUMENTS

| | | | |
|---|---|---|---|
| 5,443,492 A * | 8/1995 | Stokes et al. | 607/131 |
| 5,683,447 A * | 11/1997 | Bush et al. | 607/126 |
| 6,009,877 A * | 1/2000 | Edwards | 128/898 |
| 6,205,360 B1 | 3/2001 | Carter et al. | 607/57 |
| 6,208,882 B1 | 3/2001 | Lenarz et al. | 600/379 |
| 6,936,006 B2 * | 8/2005 | Sabra | 600/300 |
| 2002/0133148 A1 * | 9/2002 | Daniel et al. | 606/34 |
| 2005/0216073 A1 | 9/2005 | Jolly et al. | 607/137 |
| 2006/0041277 A1 * | 2/2006 | Deem et al. | 607/3 |
| 2006/0206164 A1 * | 9/2006 | Gavronsky | 607/46 |
| 2008/0228194 A1 * | 9/2008 | Westlund et al. | 606/129 |
| 2009/0036765 A1 * | 2/2009 | Espenhain | 600/373 |
| 2010/0268054 A1 * | 10/2010 | Behrend et al. | 600/373 |

* cited by examiner

ELECTRODE ARRANGEMENT AND MEASURING DEVICE FOR MEASURING THE ELECTRICAL ACTIVITY IN AN ELECTRICALLY ACTIVE TISSUE

This application is a national phase entry of Patent Cooperation Treaty Application PCT/EP2008/056944, filed Jun. 4, 2008, which is incorporated herein by reference.

FIELD OF THE INVENTION

The present invention relates to an electrode configuration and a measuring device for measuring the action current and/or the action potential of electrically active tissue, in particular, the present invention relates to a bipolar stapedius muscle electrode configuration for measuring the action potential generated upon a contraction of the stapedius muscle.

BACKGROUND ART

The human ear may be divided into the following areas: outer ear (auricle), middle ear, and inner ear. The middle ear comprises the eardrum and the auditory ossicles hammer, anvil, and stirrup. The eardrum is caused to oscillate via sound waves entering the outer ear. These oscillations may be transmitted via hammer, anvil, and stirrup to the oval window of the inner ear, by which sound oscillations may in turn be generated in the liquid of the cochlea. The hair cells projecting into the cochlea are bent by the movement of the liquid and thus trigger nerve pulses. A mechanical impedance conversion occurs in the middle ear, which allows an optimum transmission of the sound signal from the outer ear to the inner ear.

In addition, the tympanic muscle and the so-called stapedius muscle are located in the middle ear. The tympanic muscle is linked to the hammer, the stapedius muscle being connected via a tendon to the stirrup. In case of an excessively high sound pressure, which could damage the inner ear, both muscles contract reflexively, so that the mechanical coupling of the eardrum to the inner ear (and thus also the force transmission) is decreased. In this way, it is possible to protect the inner ear from excessively high sound pressures. The tensing of the stapedius muscle triggered as a result of high sound pressures is also referred to as the stapedius reflex. Medically relevant information about the functional capability of the ear may be obtained from the diagnosis of the stapedius reflex. Furthermore, the measurement of the stapedius reflex is useful for setting and/or calibrating so-called cochlear implants, because the sound energy perceived by a patient may be concluded from the measured stapedius reflex.

Using electrodes, which are brought into contact with the stapedius muscle and which relay action current and/or action potentials generated upon a contraction of the stapedius muscle to a measuring device, is known for measuring the stapedius reflex. A reliable, minimally-invasive contact of the stapedius muscle is difficult, because the stapedius muscle is situated inside a trough present in a bone and only the tendon of the stapedius muscle connected to the stirrup and its upper part are accessible from the interior of the middle ear.

Various stapedius muscle electrodes are known from U.S. Pat. No. 6,208,882. However, these only achieve inadequate contact of the stapedius muscle tissue (in particular upon muscle contraction) and are also very traumatizing.

It is therefore the object of the present invention to specify an electrode, which may be produced simply and cost-effectively, for measuring action currents and/or action potentials in electrically active tissues (preferably the stapedius muscle tissue), which, on the one hand, ensures secure but reversible fixation of the electrode in the muscle tissue and, on the other hand, traumatizes the muscle tissue as little as possible.

SUMMARY OF THE INVENTION

Embodiments of the present invention are directed to an electrode configuration that is implemented in at least two parts and has a first electrode and a fixation element, the first electrode being connected to a first, oblong electrical line, and the first electrode further comprising an elongate main body having a first end and a second end, the first electrical line being connected to the main body in the area of its second end, and means being provided for fixing the fixation element on the first electrode. The idea of the present invention comprises causing the fixation of the (first) electrode in the (stapedius) muscle tissue by a fixation element to be introduced separately, the fixation element penetrating the main body of the (first) electrode, preferably through its lateral surface, and thus fixing it (for example, on the tendon of the stapedius muscle).

In an especially preferred embodiment variant, the main body of the (first) electrode and the fixation element are implemented in such a way that the fixation element may be snapped, plugged, or screwed nearly perpendicularly into the main body of the (first) electrode (preferably at an angle between 45 and 90° to the longitudinal axis of the main body). The connection between fixation element and main body is to be reversible, i.e., able to be disengaged again. The advantage of the invention in relation to typical electrodes is that the (first) electrode does not have to have further (traumatizing) retention mechanisms because of the lateral fixation, and therefore may be implemented as very smooth running and thus minimally invasive for the tissue.

Furthermore, it is preferable for a bipolar measurement of the action potential of the tissue (stapedius muscle tissue) to occur, the fixation element being implemented as a (preferably elongate) second electrode. The action potential may thus be determined at higher local resolution, namely between two measuring points of the two electrodes. These two electrodes are preferably insulated in relation to one another (in the area in which they are not directly in contact). Preferably, at least one of the two electrodes comprises a conductive core and has an insulating sheath, the conductive core being exposed in the area of the desired measuring point in each case. The exposed areas are located outside the region in which the two electrodes contact directly for the fixation.

The main body is preferably implemented essentially in the form of a half hollow cylinder (or a half cylinder). A main body in the form of a half hollow cylinder is understood to mean a hollow-cylindrical main body which is open (not only at the head end, but rather also) along its longitudinal axis, the lateral surface being implemented in the form of a circular arc in cross-section, and the center point angle of the circular arc being between 120° and 240°, preferably between 165° and 195°, and especially preferably 180°. The radius associated with the circular arc is preferably between 0.25 and 1.5 mm. The wall thickness of the lateral surface is preferably between 50 and 500 µm.

Furthermore, it is preferable for the main body to be implemented from an electrically conductive rigid material (preferable bending rigidity 200-600 N mm$^2$, more preferably 400-500 N mm$^2$, and especially preferably 450 N mm$^2$). In a preferred embodiment variant, the electrically conductive main body is sheathed by insulation (with the exception of the exposed area—preferably in the area of the pointed first end).

The main body preferably has an electrically insulated through opening on its lateral surface or on its external surface. The cross-section of the through opening corresponds to the cross-section of the second electrode in such a way that the second electrode may be inserted, snapped, plugged, or screwed into the through opening. It is made possible according to the invention by the corresponding dimensions of through opening of the first electrode and the cross-section of the second electrode that the first electrode may be fixed temporarily or permanently and securely by inserting, snapping, plugging, or screwing the second electrode into the through opening. In particular, the fixation may be disengaged easily by reverse withdrawal of the second electrode, so that both electrodes may be withdrawn easily after the measurement of the action potential/current. Because no further fixation elements are provided on the electrodes according to the invention, a measurement of the tissue (muscle) reflex may be performed in a minimally invasive way.

The lateral extension of the through opening is preferably between 101% and 110% of the lateral extension of the second electrode. Sufficient play for inserting/withdrawing the second electrode is thus ensured, but secure fixation of the electrode is also ensured. The through opening preferably has an electrical insulation layer on its inner surface, so that a short circuit is prevented in the contact area of the electrodes. The insulation layer preferably comprises insulation ceramic or sapphire and has a thickness between 10 and 30 µm. Alternatively, it is possible that the second electrode has electrical insulation in the area in which it contacts the through opening of the main body. This electrical insulation preferably comprises silicone or polyurethane.

The second electrode preferably has a diameter of 0.2 mm to 2 mm. The main body preferably has a length of 0.8 mm to 1.4 mm. The second electrode preferably has a length of 1.5 mm to 3.0 mm. The preferred dimensions are particularly suitable so that the first electrode may be guided inside the channel located between tendon/stapedius muscle and bone while preserving tissue. In particular, the main body, in the form of a half hollow cylinder, of the first electrode may (half) enclose the tendon of the stapedius muscle and thus be advanced reliably to the muscle (as if on a guide). The second electrode used for fixation is preferably inserted perpendicularly thereto into the tissue (tendon).

In the area of its first end, the main body preferably has a bevel which has an angle between 30° and 60° to the longitudinal axis of the main body. A tissue-preserving insertion of the first electrode is thus made possible.

If the fixation element comprises an electrically insulating material (i.e., no second electrode is provided), the first electrode may be implemented as a monopolar electrode. The first electrical line is then preferably connected in a formfitting and/or friction-locked way to a voltmeter or a current meter. The voltmeter is preferably designed to measure the electrical potential applied to the first electrode in relation to a reference potential or zero potential.

In an especially preferred embodiment variant, it is provided that the first electrode and the second electrode are implemented as a bipolar measuring configuration. Both the first electrical line and also the second electrode are then connected to a voltmeter/current meter and the voltmeter is designed to measure the electrical potential applied between the first electrode and the second electrode. The voltmeter is preferably designed to measure the electrical potential applied between the first electrode and the second electrode in the range from +100 mV to −100 mV (preferably +40 mV to −90 mV).

In addition to the first electrode, the second electrode may also be connected to a second electrical (supply) line, the supply lines being connected to the (volt or current) meter. The electrodes must have a certain intrinsic rigidity in the distal area, to be able to be held and guided using known surgical instruments. The supply lines are preferably implemented as flexible.

The first electrode may be completely electrically conductive, as long as the supply is electrically insulated in relation to the surrounding tissue. Of course, insulation must be provided in relation to the second electrode for the bipolar case. For this purpose, the second electrode or the through opening (hole) of the first electrode may be partially insulated.

According to a further aspect of the invention, a method is disclosed for determining the action current and/or the action potential of human, electrically active tissue, in which a first electrode (provided with the above-mentioned features) is inserted from a first direction into the active tissue and a fixation element (preferably a second electrode provided with the above-mentioned features) is inserted separately from a second direction into the active tissue, the fixation element (preferably the second electrode) being plugged, snapped, or screwed into the first electrode. The fixation element (preferably the second electrode) is preferably plugged, snapped, or screwed in at an angle of 70°-90° to the longitudinal axis of the first electrode.

In the case of the measurement of action potential of the stapedius muscle, the first electrode is firstly inserted directly into the muscle tissue. In the case of the stapedius muscle, this is performed along the tendon of the muscle, which is thus used as a guide. The second electrode is used for the fixation and is accordingly inserted separately and perpendicularly to the longitudinal axis of the first electrode and the tendon. The muscle is accessible in the surgical field. In order to hit the through opening, the tendon may be used as an orientation. As a second variant, the fixation may be performed not in the muscle, but rather outside on the tendon. In this case, the through opening is visible and easy to hit. The second electrode may nonetheless be used as a reference electrode for a bipolar potential derivation. If further tissue is to be penetrated for the application, this is unimportant for the function. All electrodes and supply lines are preferably electrically insulated in relation to other tissues or bodily fluids.

DETAILED DESCRIPTION OF SPECIFIC EMBODIMENTS

Figure 1:
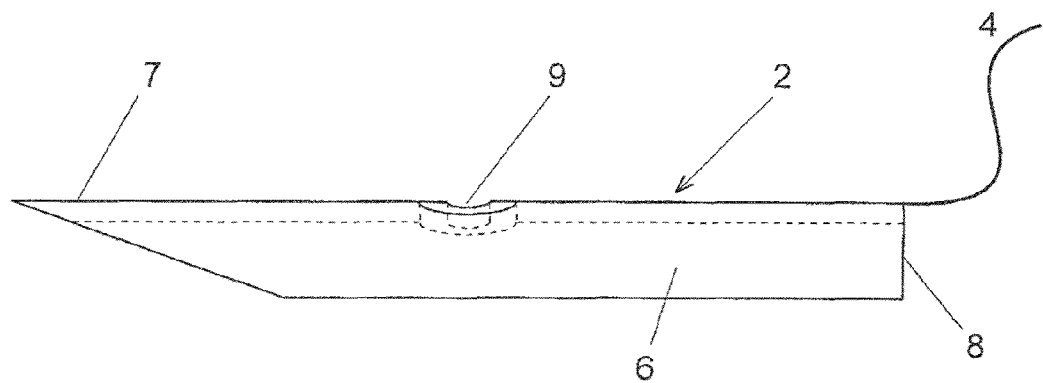
FIG. 1 shows the first electrode of a two-part electrode configuration according to the invention in a schematic, sectional illustration.
Figure 2:
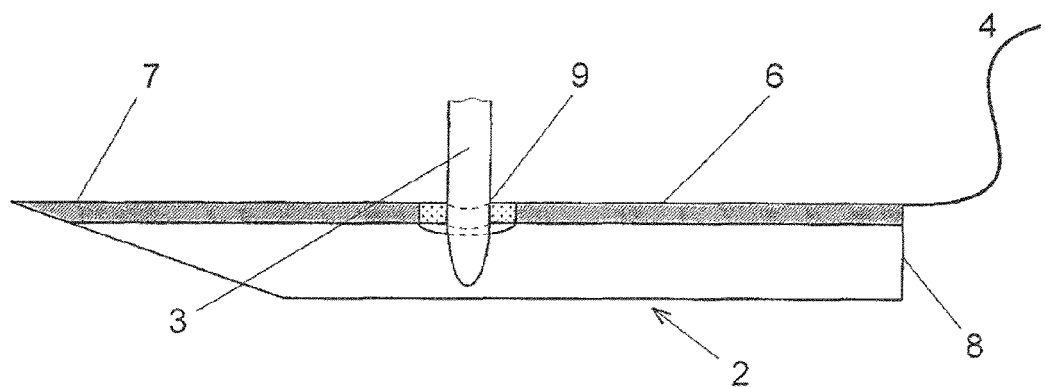
FIG. 2 shows an electrode configuration according to the invention in a schematic, sectional illustration, in which the second electrode is plugged into the first electrode for the fixation.
Figure 3:
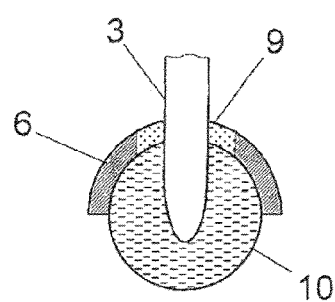
FIG. 3 shows the electrode configuration according to the invention from FIG. 2 in a schematic sectional illustration perpendicular to the longitudinal axis of the first electrode.
Figure 4:
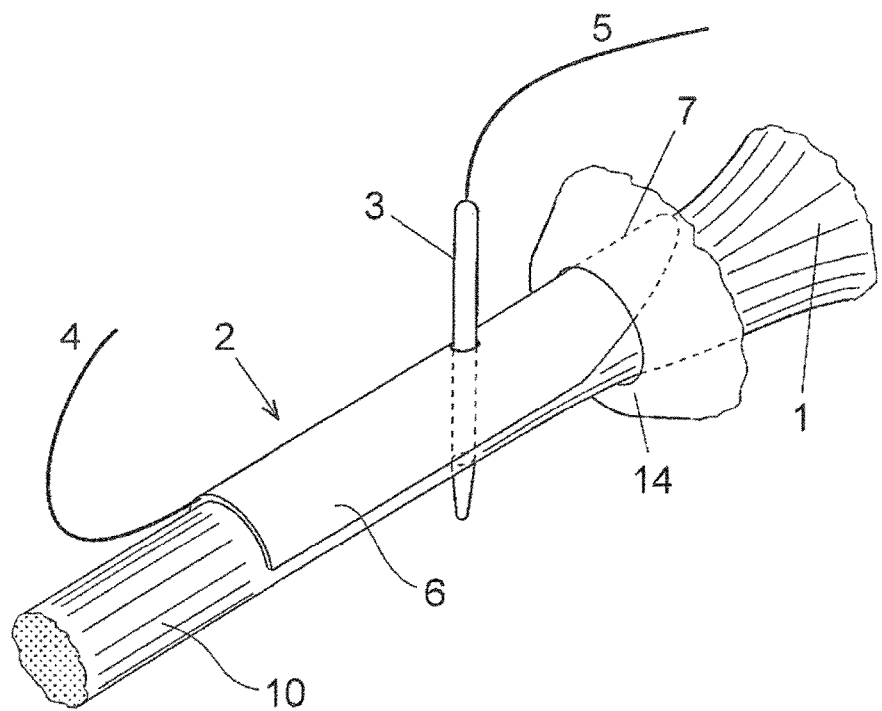
FIG. 4a shows the electrode configuration according to the invention, fastened on a stapedius muscle tendon, in a perspective illustration.
FIG. 4b shows the electrode configuration according to the invention, fastened on a stapedius muscle tendon, in a sectional illustration.
Figure 4:
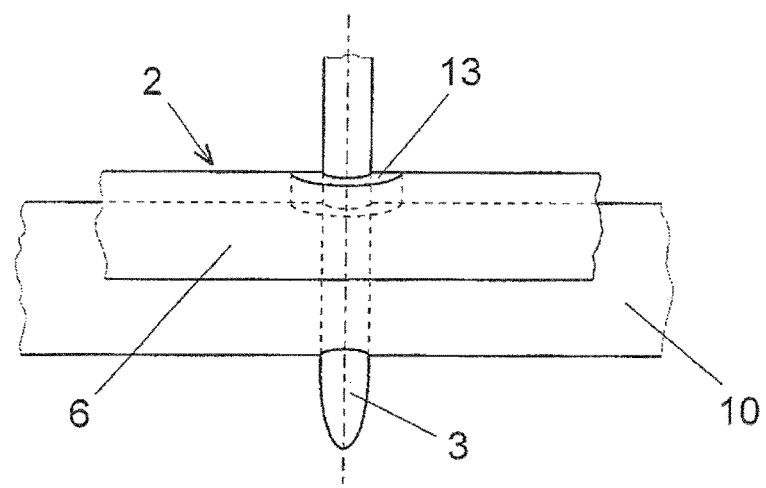
Figure 5:
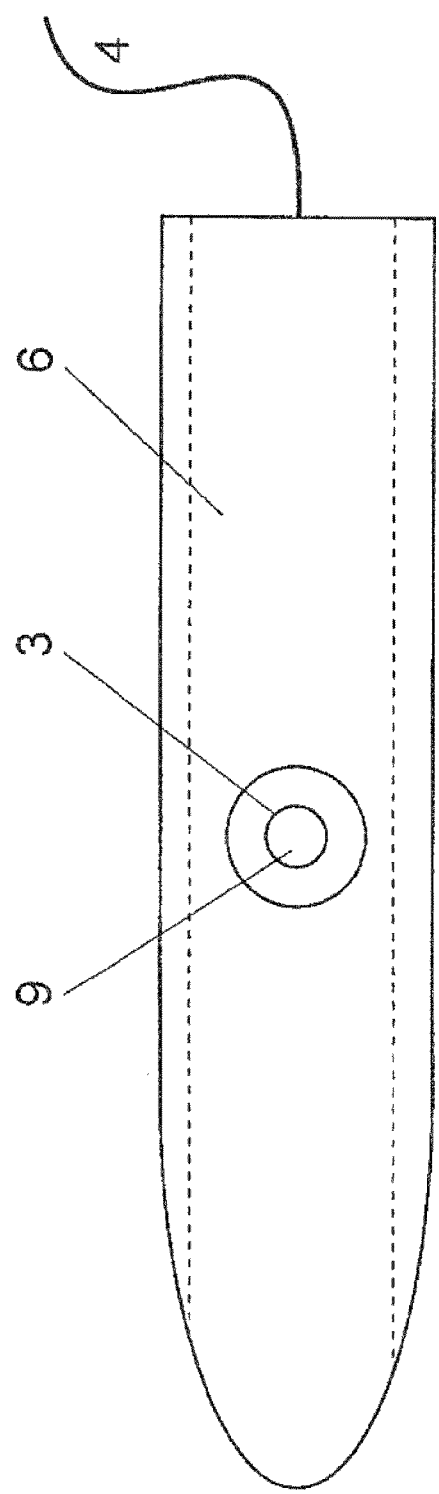
FIG. 5 shows the electrode configuration according to the invention from FIG. 2 in a top view.

FIG. 1 shows a (first) electrode 2 of the electorate configuration according to the invention in a schematic, sectional illustration. According to the invention, the first electrode 2 comprises an elongate main body 6, which, in an especially preferred embodiment variant, is implemented in the form of a half hollow cylinder (hollow cylinder open along its longitudinal axis having a center point angle of approximately 180°) made of a conductive material. Furthermore, it is provided that an electrical supply line 4 is connected to the main body 6 in the area of the second end 8. The electrical supply line 4 is preferably electrically insulated. In the area of the first end 7, the hollow-cylindrical main body 6 preferably has a bevel in the angle range from 30° to 60°. Because of its oblong shape, it is only possible to guide the main body 6 through tissue 1 along its longitudinal axis.

Figure 6:
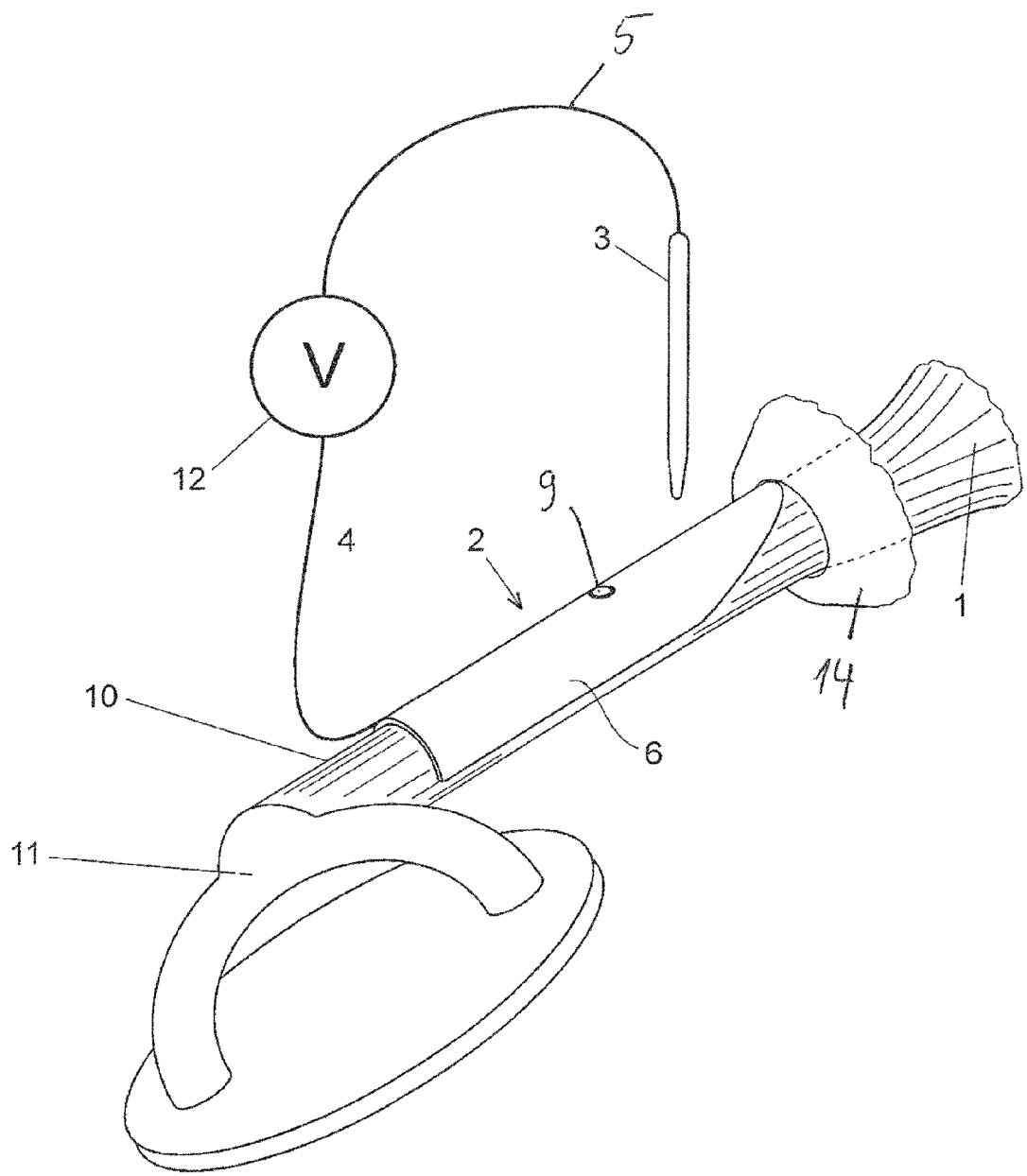
FIG. 6 shows a measuring device according to the invention in a schematic illustration, the first electrode being inserted into the stapedius muscle and the second electrode being inserted into the tendon (before and after the fixation/measurement).
Figure 7:
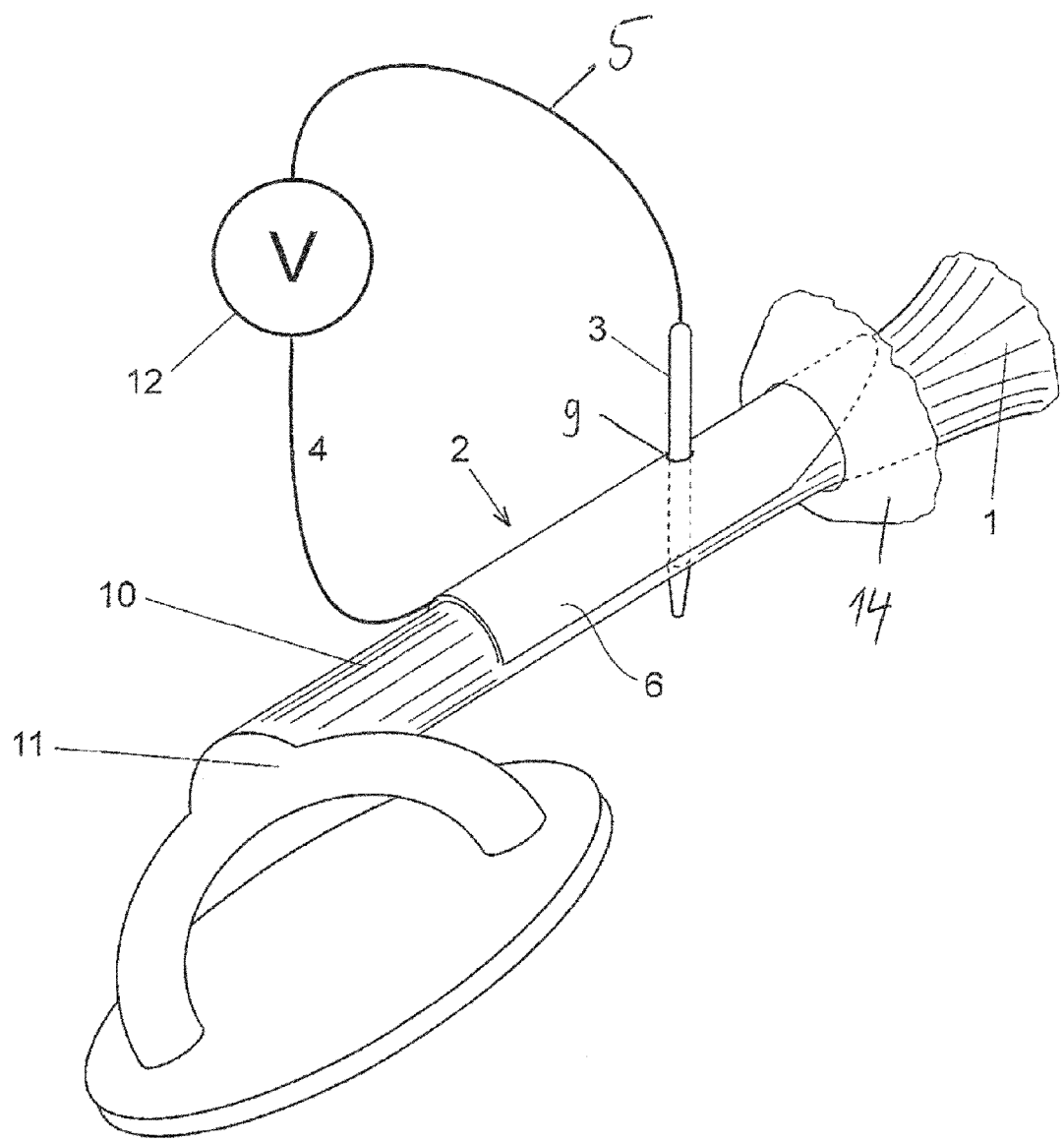
FIG. 7 shows a measuring device according to the invention in a schematic illustration, the first and second electrodes being fixed in the stapedius muscle (during the measurement).

To ensure secure fixation of the main body 6 in electrically active tissue 1, it is provided according to the invention that the main body 6 is fixed using a separate fixation element 3 to be inserted (situated) at an angle in relation to the longitudinal axis of the main body 6. In an especially preferred embodiment variant (FIGS. 2 through 7), the fixation is implemented by a second electrode 3, which is plugged into a through opening 9 of the main body 6 in an especially preferred embodiment variant. A bipolar measuring configuration may thus be provided, the first electrode 2 being connected via the electrical supply line 4 and the second electrode 3 being connected via the electrical supply line 5 to a voltmeter 12 in each case (FIGS. 6 and 7). Because of the existing mobility of the main body 6 along its longitudinal axis inside the muscle tissue 1, secure fixing is achieved using the second electrode 3 by plugging it into the through opening 9 at a finite angle (preferably)60°-90° to the longitudinal axis of the main body 6, because the plugged-in second electrode 3 blocks the movement of the main body 6 along its longitudinal axis. It is especially preferable to plug the second electrode 3 perpendicularly into the through opening 9 of the main body 6. Alternatively, it is also possible to produce a screw or catch connection between the electrodes 2, 3.

To measure the action potential within the tissue, it is necessary for the electrodes 2, 3 to be electrically insulated from one another in the area in which they are in direct contact. Thus, for example, it is possible that the main body 6 is implemented as electrically conductive and is only electrically insulated in the area 13 of its through opening 9. If only the tip (first end 7) of the main body 6 is located in the muscle tissue 1 (FIGS. 4b and 7), however, it is advantageous to also insulate the remaining main body 6 (except in the area of the first end 7). The electrical supply line 4 (and/or the electrical supply line 5) also must always be electrically insulated in relation to surrounding tissue. Alternatively to the insulation of the main body 6 in the area of the through opening 9, it is possible to insulate the electrode 3 in the area in which it is plugged into the through opening 9. The second electrode 3 and/or its electrical supply 5 and the first electrode 2 and/or its electrical supply 4 (FIG. 4a) must be electrically insulated in an area running to the meter 12 in any case, to be able to implement a punctual measurement of the action potential in the stapedius muscle 1-FIG. 7.

FIGS. 6 and 7 show a possible use of the electrode configuration according to the invention for measuring the action potential of the stapedius muscle 1. For this purpose, it is provided that the main body 6 of the first body 2 is moved using appropriate surgical instruments along the tendon 10, which connects the stapedius muscle 1 to the stirrup 11, into the stapedius muscle 1 (see 6 and 7 and also FIG. 4a). The electrode main body 6 may be pushed in the channel (existing between the tendon 10 and the bone 14 surrounding the stapedius muscle 1) (FIG. 7). The second electrode 3 is pushed into the stapedius muscle 1 (alternatively through the through opening 9 and into the tendon 10) separately and (nearly) perpendicularly to the feed direction of the electrode main body 6 according to the invention. Both electrodes 2, 3 are inserted far enough that the first end 7 of the main body 6 at least partially contacts the stapedius muscle 1 and the second electrode 3 engages in the through opening 9 of the electrode main body 6 (FIG. 7) and thus blocks a movement of the electrode body 6 along its longitudinal axis. A reliable determination of the action potential via the connected meter 12 is now possible. However, the first electrode 2 does not have to be completely inserted into the stapedius muscle 1; alternatively, it is also possible to insert the electrode main body 6 only partially into the stapedius muscle 1 (FIGS. 4a and 7). In this case, the electrode main body 6 is to be electrically insulated (except in the area of the front end 7). The second electrode 3 may now be inserted into the through opening 9 outside the stapedius muscle 1 (in the area of the tendon 10) and fix the electrode main body 6 for measuring the action potential. The inner area 13 of the through opening 9 is preferably provided with insulation, so that a short-circuit may be avoided between first electrode 2 and second electrode 3 (FIG. 4b).

Although various exemplary embodiments of the invention have been disclosed, it should be apparent to those skilled in the art that various changes and modifications can be made which will achieve some of the advantages of the invention without departing from the true scope of the invention.

LIST OF REFERENCE NUMERALS 1 electrically active tissue/muscle
2 first electrode
3 fixation element/second electrode
4 first electrical line
6 main body
7 first end of the main body
8 second end of the main body
9 through opening
10 tendon
11 stirrup bone
12 voltmeter/current meter
13 insulation
14 bone

What is claimed is:

1. An electrode for measuring electrical activity of tissue, the electrode comprising:
   a sensing electrode having an elongate electrode body forming a partial hollow half cylindrical section having a proximal end, a distal end, and a curved inner surface configured to partially enclose a curved outer surface of the tissue and with:
   i. a penetrating end at the distal end for insertion into the tissue to sense electrical activity of the tissue, and ii. a base end at the proximal end that is coupled to an electrical connection wire for communicating the sensed electrical activity away from the sensing electrode; and a fixation element that penetrates through an electrode opening in the elongate electrode body into the tissue partially enclosed by the curved inner surface of the partial hollow half cylindrical section of the electrode body to hold the penetrating end of the sensing electrode in position in the tissue.

2. An electrode according to claim 1, wherein the fixation element includes a secondary sensing electrode that also senses electrical activity of the tissue.

3. An electrode according to claim 2, wherein the sensing electrode and the secondary sensing electrode form a bipolar electrode sensing arrangement.

4. An electrode according to claim 1, further comprising:
an electrical insulation layer where the fixation element penetrates the electrode body for electrically isolating the fixation element from the electrode body.

5. An electrode according to claim 4, wherein the insulation layer is ceramic, sapphire, $A_2O_3$, $TiO_2$, or glass.

6. An electrode according to claim 4, wherein the insulation layer has a thickness between 10 μm and 30 μm.

7. An electrode according to claim 1, including an insulation layer covering at least a portion of the sensing electrode or the fixation element.

8. An electrode according to claim 7, wherein the insulation layer is silicone or polyurethane elastomer.

9. An electrode according to claim 1, wherein the fixation element is formed of electrically insulating material and the sensing electrode acts as a monopolar sensing arrangement.

\* \* \* \* \*

UNITED STATES PATENT AND TRADEMARK OFFICE
CERTIFICATE OF CORRECTION

PATENT NO. : 8,725,227 B2  Page 1 of 1
APPLICATION NO. : 12/601156
DATED : May 13, 2014
INVENTOR(S) : Behrend et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 968 days.

Signed and Sealed this

Twenty-ninth Day of September, 2015

Michelle K. Lee
*Director of the United States Patent and Trademark Office*